United States Patent [19]
Levin

[11] Patent Number: 5,643,313
[45] Date of Patent: Jul. 1, 1997

[54] LAPAROSCOPIC TISSUE COMPRESSOR AND EXTRACTOR

[76] Inventor: John M. Levin, 412 Fairview Rd., Narbeth, Pa. 19072

[21] Appl. No.: 508,595

[22] Filed: Jul. 28, 1995

[51] Int. Cl.$^6$ .................................. A61M 29/00
[52] U.S. Cl. .............. 606/198; 604/264; 606/191
[58] Field of Search .............. 606/1, 106, 10 B, 606/110, 113, 127, 128, 198, 159; 128/751; 604/264

[56] References Cited

U.S. PATENT DOCUMENTS

| | | | |
|---|---|---|---|
| 4,509,517 | 4/1985 | Zibelin | 606/127 |
| 4,611,594 | 9/1986 | Grayhack et al. | 606/127 |
| 4,691,705 | 9/1987 | Okada | 606/127 |
| 4,741,335 | 5/1988 | Okada | 606/127 |
| 4,811,735 | 3/1989 | Nash et al. | 606/128 |
| 4,899,729 | 2/1990 | Gill et al. | 606/198 |
| 5,139,511 | 8/1992 | Gill et al. | 606/198 |
| 5,147,371 | 9/1992 | Washington et al. | 606/127 |
| 5,176,688 | 1/1993 | Narayan et al. | 606/128 |
| 5,190,561 | 3/1993 | Graber | 606/127 |
| 5,197,968 | 3/1993 | Clement | 606/128 |
| 5,330,483 | 7/1994 | Heaven et al. | 606/114 |
| 5,370,647 | 12/1994 | Graber et al. | 606/127 |
| 5,464,408 | 11/1995 | Duc | 606/108 |

FOREIGN PATENT DOCUMENTS

| | | | |
|---|---|---|---|
| 2945237 | 5/1981 | Germany | 606/127 |
| 1228837 | 5/1986 | U.S.S.R. | 606/127 |
| WO92/11816 | 7/1992 | WIPO | 606/128 |

Primary Examiner—Michael Powell Buiz
Assistant Examiner—Patrick W. Rasche
Attorney, Agent, or Firm—Caesar, Rivise, Bernstein, Cohen & Pokotilow, Ltd.

[57] ABSTRACT

An apparatus for compressing and extracting internal body tissues wherein the apparatus is insertable through a trocar device and encompasses the tissue to be removed while compressing the tissue in situ outside of the trocar or of any incision access device, and then being removable from the trocar/incision device.

2 Claims, 7 Drawing Sheets

LAPAROSCOPIC TISSUE COMPRESSOR AND EXTRACTOR

SPECIFICATION

1. Field of the Invention

This invention relates generally to the field of medical devices, more particularly, to tissue compressors/extractors that can be used during laparoscopic surgery for compressing tissue internally within the patient before the tissue is extracted through the trocar.

2. Background of the Invention

The removal of body parts during laparoscopic surgery is typically accomplished with an instrument that is fed through a trocar and wherein the instrument has a means for seizing the body part. Once the body part is captured by the instrument, the instrument/body part is pulled back up through the trocar. This pulling action tends to compress the body part into the general tubular configuration of the trocar, if the body part can even be compressed. Where the body part cannot pass through the trocar, an incision is necessary to remove the body part, thereby defeating the advantages of the laparoscopic surgery.

The following U.S. Patents describe various types of tissue extractors and/or compressors: 5,370,647 (Graber et al.); 5,330,483 (Heaven et al.); 5,176,688 (Narayan et al.); 5,147,371 (Washington, deceased et al.); 5,190,561 (Graber); 4,811,735 (Nash et al.); 4,741,335 (Okada); 4,691,705 (Okada); 4,611,594 (Graycheck et al.); 4,509,517 (Zibelin).

The apparatus disclosed by Graber et al. and Graber is a tissue extractor which is passed down through a cannula (i.e., trocar) and utilizes a retractable skirt for enveloping a body part to be removed. The skirt is controlled by the surgeon and is used in conjunction with a forceps that is passed down through the center of the retractable skirt for grasping the body part. Once the body part is trapped in the skirt, the extractor/forceps/cannula assembly is removed from the puncture orifice.

The apparatus disclosed by Heaven et al. is a thermally-activated specimen reduction device for use during laparoscopic surgery. The device comprises a tubular-shaped, thermally-responsive material which can be positioned to encompass a body part. The material comprises fibers that, when heated (e.g., application of a hot liquid much greater than body temperature or application of electrical current), shrink and thereby crush the encompassed body part sufficiently to allow the passage of the material/body part unit through the trocar.

The apparatus disclosed by Washington (now deceased) et al. is an apparatus for removing gallstones and tissue during surgery. In particular, this device comprises an elongated tube having a collapsible bag at the distal end whose opening can be closed by the surgeon once the gallstones are placed inside the bag. The bag can then be pulled up into the tube to remove the gallstones from the body.

The apparatus disclosed in both Okada patents is a calculus crushing apparatus that includes a collapsible basket which is inserted into the body. The collapsible basket is coupled to one end of an inner one of two flexible sheaths. The flexible sheaths are displaceable with respect to one another and are each controllable by the surgeon. Upon capturing the body part (to be removed) in the basket, respective displacement of the flexible sheaths causes the basket to collapse and impact of the collapsed basket with hardened end of the outer sheath crushes the body part.

The apparatus disclosed by Graycheck et al. is a device for containment of calculi within a collapsible cage comprising, among other things, wire strands that captures the calculi and allows it to be pulled into an expandable hollow catheter or simply held in place so that the calculi can then be either more safely extracted or can be fragmented.

The apparatus disclosed by Narayan et al. is a device for capturing a kidney stone within a basket, comprising a plurality of wires, that stabilizes the stone so that a reciprocating shaft can fragment the stone into pieces. The wires are then drawn together to enclose and then withdraw the fragmented stone.

The apparatus disclosed by Zibelin is a kidney stone instrument that is inserted into the body for grasping, crushing and then removing the crushed stones.

The apparatus disclosed by Nash et al. is also a kidney stone instrument having a cutting head that is retractable within a catheter and extendable for deploying at least one blade that can be rotated to destroy the kidney stone. This device also utilizes a shroud to aid in directing the stone toward the blades.

However, there remains a need for a device that can be inserted into a trocar, encompass an internal body tissue, compress it into a small enough volume outside of the trocar (or a trocar-like incision tube) to achieve the compression, and permit the removal of the internal body tissue.

OBJECTS OF THE INVENTION

Accordingly, it is the general object of this invention to provide an apparatus and a method of use which addresses the aforementioned needs.

It is a further object of this invention to provide an apparatus that can compress internal body tissue outside of the trocar into which the apparatus is inserted.

It is yet another object of this invention to provide an apparatus that can compress internal body tissue outside of any associated elongated tube.

It is still yet a further object of this invention to provide an apparatus that can compress internal body tissue without the use of a thermally-sensitive or chemically sensitive enclosure.

It is still yet another object of this invention to provide a device for removing gallbladders with the stones in them, for removing sections of bowels or appendices wherein the pathology presents a problem because it makes these body parts less compressible than healthy parts (e.g., due to the presence of inflammation, tumors, etc.)

It is even yet a further object of this invention to provide an apparatus that can compress the internal body tissue without the need for cutting, fragmenting or pulverizing means.

SUMMARY OF THE INVENTION

These and other objects of the instant invention are achieved by providing an apparatus for compressing and extracting internal body parts to be removed from a patient. The apparatus comprises means for encompassing and compressing an internal body part to be removed. The encompassing and compressing means includes overlapping sections that are movable relative to each other. These overlapping sections form a variable-sized chamber having walls of sufficient rigidity for compressing the body part to a size permitting the removal of the compressed body part from the body.

DESCRIPTION OF THE DRAWINGS

Other objects and many of the attendant advantages of this invention will be readily appreciated as the same becomes better understood by reference to the following detailed description when considered in connection with the accompanying drawings wherein.

DESCRIPTION OF THE PREFERRED EMBODIMENT OF THE INVENTION

Figure 1:
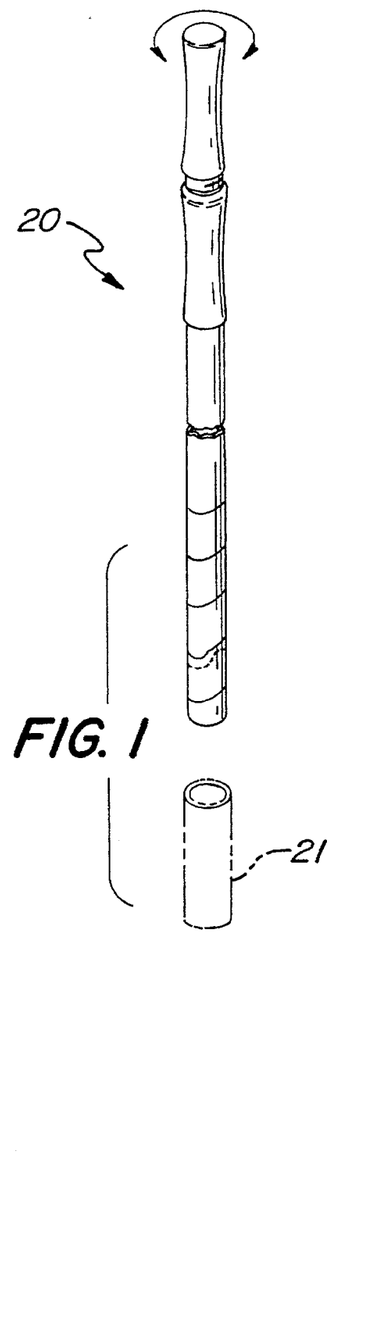
FIG. 1 is a diagram of the preferred embodiment of the tissue compressor/extractor.

Referring now in greater detail to the various figures of the drawing wherein like reference characters refer to like parts, a tissue compressor/extractor (hereinafter "TCE") constructed in accordance with the present invention is shown generally at 20 in FIG. 1. The TCE 20 is a self-contained device for encompassing and compressing an internal body part. As also shown in FIG. 1, the TCE 20 is insertable through a trocar 21. In particular, as shown most clearly in FIG. 2, the TCE 20 comprises a rotatable upper portion 22 and a stationary lower housing 24.

Figure 3:
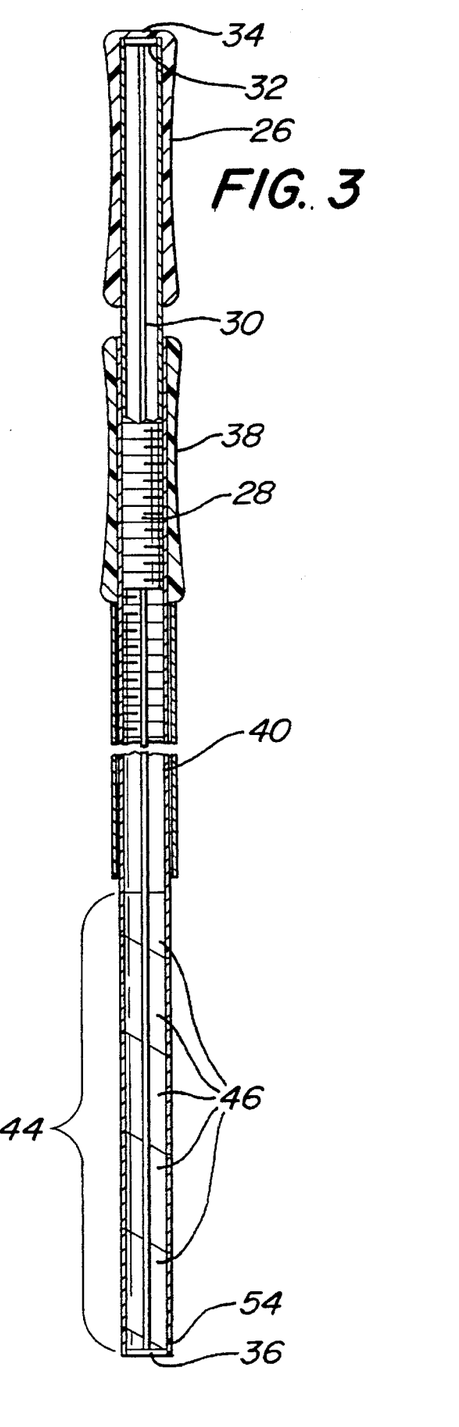
FIG. 3 is a cross-sectional view taken along line 3—3 of FIG. 2.

As shown more clearly in FIG. 3, the upper portion 22 comprises a hollow handle grip 26 in which the upper end of a cylinder 28, whose outer surface comprises threads, is secured. A control rod 30 is secured to a disk 32 which, in turn, is fixedly secured to the inside surface of the top wall 34 of the handle grip 26. The lower end of the control rod 30 is fixedly secured to another disk 36. Hence, the rotation of the handle grip 26 by the surgeon causes the disk 36 to rotate.

Figures 4, 5:
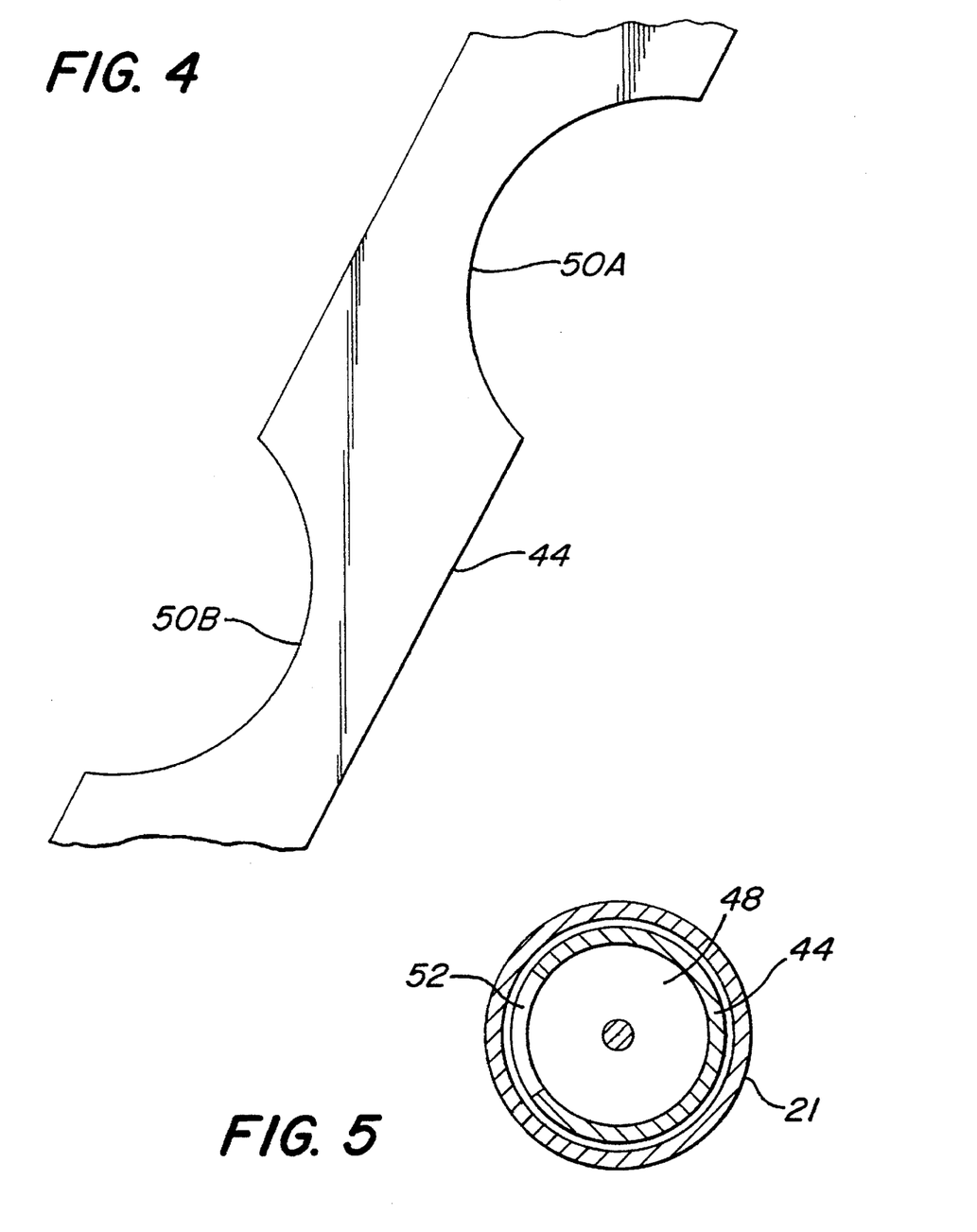
FIG. 4 is a view of the unwound overlapping helix of the tissue compressor/extractor.
FIG. 5 is a cross-sectional view taken approximately along line 5—5 of FIG. 2.

As shown more clearly in FIG. 3, the stationary lower housing 24 comprises a hollow, fixed handle grip 38 having a lower end that is fixedly secured over the upper portion of a hollow cylinder 40. The internal surface of the fixed handle grip 38 includes threads 42 for receipt of the threaded cylinder 28, as will be discussed later. Attached to the lower end of the hollow cylinder 40 is a helically-wound, single layer of material 44. This helically-wound single layer of material 44 forms overlapping surfaces 46 that define a cylindrical chamber 48 (FIG. 5) within these overlapping surfaces 46. FIG. 4 is a depiction of this single layer of material 44 in an unwound condition. In addition, at predetermined locations along opposing edges of the single layer of material 44 are cut-out portions 50A and 50B that form an aperture 52 (FIG. 5) in the overlapping surfaces 46 whenever the single layer of material 44 is wound to a predetermined position. Further winding beyond this predetermined position causes the overlapping surfaces 46 to misalign these cut-out portions 50A and 50B with respect to each other, thereby eliminating the aperture 52. The purpose of the aperture 52, as will be discussed in detail later, is to permit the entry of an internal body part to be compressed inside the cylindrical chamber 48 and then extracted with the TCE 20 from the body.

Figure 2:
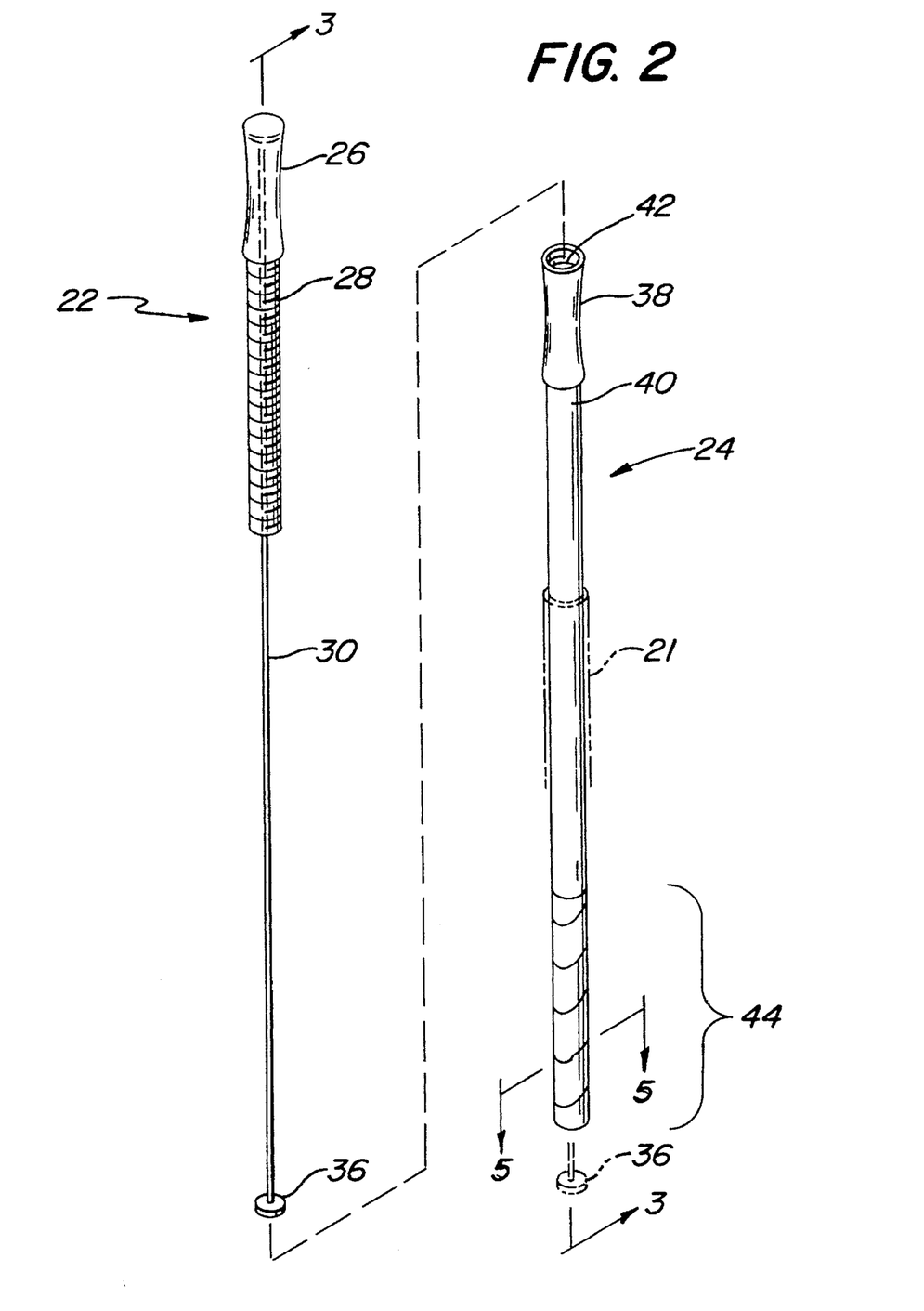
FIG. 2 is an exploded view of the tissue compressor/extractor.

As shown in FIGS. 2–3, the TCE 20 is assembled by inserting the rotatable upper portion 22 into the stationary lower housing 24 and engaging the threaded hollow cylinder 28 with the threads 42 inside the lower fixed handle grip 38. Furthermore, the lower end 54 of the helically-wound, single layer of material 44 is fixedly secured around the periphery of the disk 36.

Operation of the TCE 20 is as follows: With the TCE 20 assembled as described previously and after the TCE's 20 insertion through a trocar 21 (FIG. 2), the overlapping surfaces 46 project out from the bottom of the trocar 21. The surgeon then grasps the handle grip 26 with one hand while holding the fixed handle grip 38 with the other hand. As the surgeon rotates the grip 26 counterclockwise, the control rod 30 is rotated counterclockwise, thereby causing the disk 36 to wind the single layer of material 44. The threaded engagement of the cylinder 28 inside the fixed handle grip 38 applies an opposing force to the helically-wound material's 42 tendency to unwind, thereby alleviating the surgeon having to apply a constant winding force to maintain a desired chamber 48 diameter.

As such, the surgeon's first task is to properly wind the TCE 20 in order to form the aperture 52 in the overlapping surfaces 46. Once the aperture 52 is formed, the surgeon maneuvers the TCE 20 so that the internal body part (not shown) is inserted through the aperture and fully contained within the chamber 48. Once the body part to be compressed is encompassed within the chamber 48, the surgeon then rotates the handle grip 26 to cause the cylindrical chamber 48 to become continuously smaller in diameter, thereby compressing/crushing the body part disposed within the chamber 48. It should be understood that this single layer of material 44 is of a sufficient rigidity that permits its winding to compress a large variety of materials confined inside the chamber 48.

Once the surgeon has compressed the body part to a small enough size, the TCE 20, containing the compressed body part, is pulled up through the trocar 21.

It should be noted at this juncture that the use of a plurality of helically wound layers forming overlapping surfaces could be substituted for the single layer of helically-wound material 44 forming overlapping surfaces 46 since the former is within the scope of the broadest aspect of this invention.

Figures 6, 7:
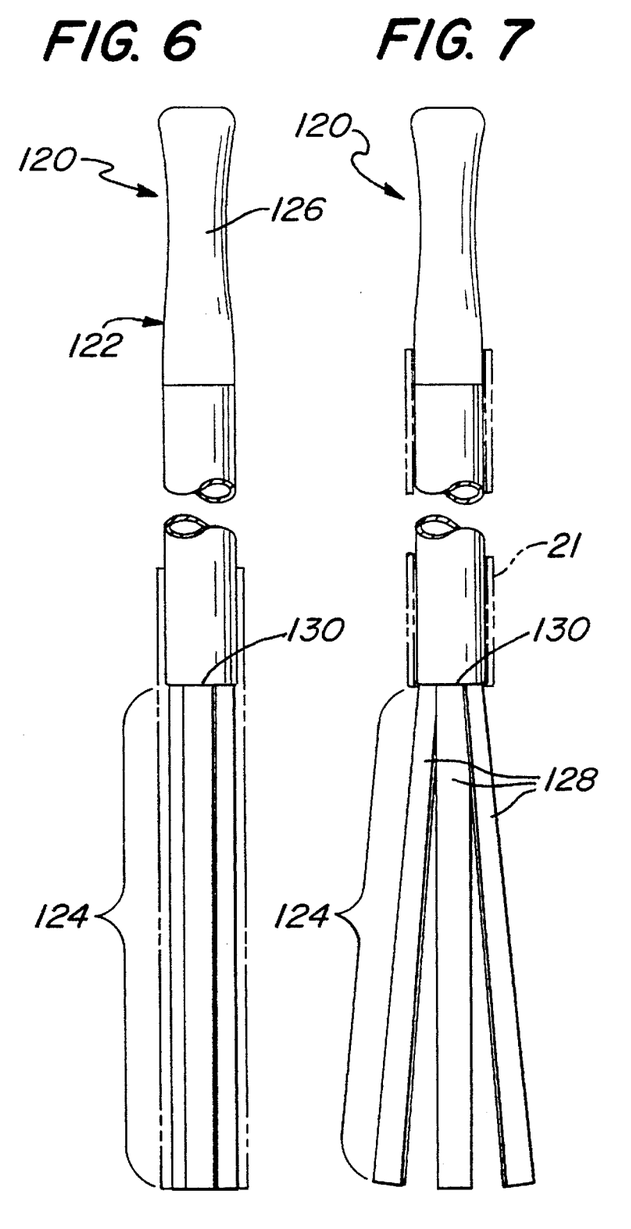
FIG. 6 is a diagram of a second embodiment of the present invention using overlapping straight slats.
FIG. 7 is a diagram of the second embodiment shown in an open condition.
Figures 8, 9:
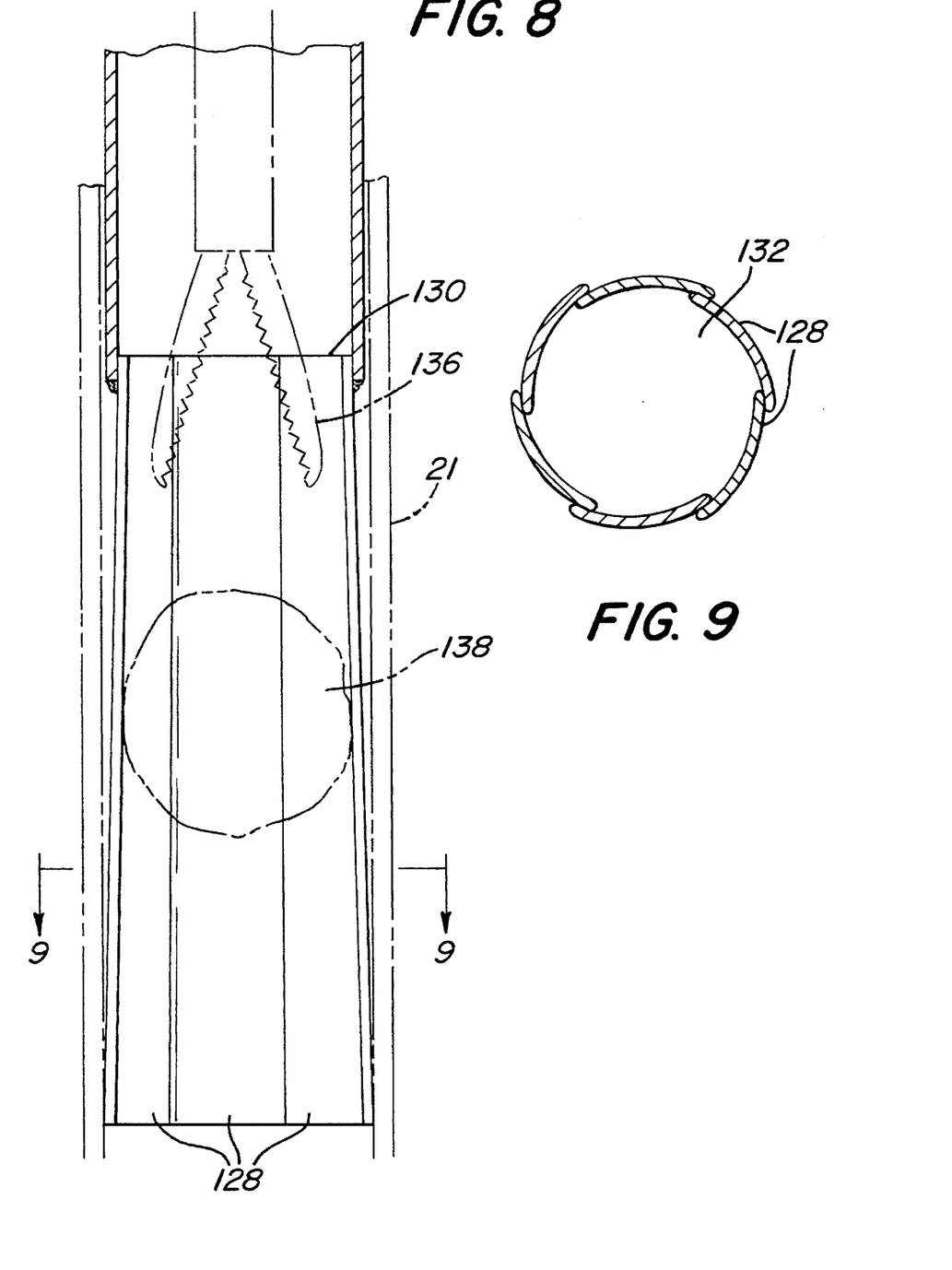
FIG. 8 is an enlarged cross-sectional view of FIG. 6 showing the insertion of a retrieval device into the second embodiment for retrieving the part to be compressed.
FIG. 9 is a cross-sectional view of FIG. 8 taken along line 9—9.

A second embodiment of the present invention is shown at 120 in FIGS. 6–7. The TCE 120 comprises a hollow cylindrical upper portion 122 and a slatted lower portion 124 that is also insertable through a trocar 21. The upper portion 122 comprises a handle grip 126 with which the surgeon grasps and controls the TCE 120. The slatted lower portion 124 comprises a plurality of slats 128, each of which are coupled to the lower end 130 of the hollow cylindrical portion 122 at their respective upper ends; The respective lower ends of each slat 128 are free. Each slat 128 is coupled to the lower end 130 to form a stiff hinge, i.e., whenever there is no exterior force applied to the slats 128, the slats 128 assume a "skirt" orientation as shown in FIG. 7. On the other hand, whenever the slatted lower portion 124 is inserted into the trocar 21, the slats 128 are driven inward to form a cylindrical chamber 132 wherein the sides of the slats overlap, as shown in FIGS. 6 and FIG. 9.

Operation of the TCE 120 is as follows: The free ends of the slats 128 are gathered by the surgeon who then inserts the TCE 120 into the trocar 21 using the handle grip 126. As the slatted lower portion 124 is passed down through the trocar 21, the slats 128 are confined to the cylindrical orientation shown in FIG. 6. As the surgeon continues to insert the TCE 120, the slats 128 begin to splay outward into the "skirt" configuration shown in FIG. 7. When the entire slatted lower portion 124 clears the lower end of the trocar 21, the slats 128 are splayed at their maximum orientation. At this point, the surgeon can position the opening 134 of the "skirt" over the body part (not shown) to be removed. As shown in FIG. 8, once this is accomplished, the surgeon then inserts a retrieval means 136 (e.g., clamp or forceps) through the hollow upper portion 122 to grasp the body part 138 to be removed and positions the body part 138 inside the "skirt" at a location where the body part 138 is lodged within the skirt. The surgeon then disengages the retrieval means 136 from the body part 138 and removes the retrieval means 136 from the TCE 120. The surgeon then pulls upward on the handle grip 126 which disposes the lower end 130 of the hollow cylindrical portion 122 inside the trocar 21, thereby causing the slats 128 to be driven inward into a cylindrical orientation forming the cylindrical chamber 132 (FIG. 9) and thereby compressing the body part 138 inside the slatted lower portion 124. It should be understood that each of the slats 128 is of a sufficient rigidity that permits the inward movement of all of the slats to compress a variety of materials confined therein. With the body part 138 compressed to the diameter of the cylindrical chamber 132, the body part 138 can then be removed with the TCE 120 through the trocar 21.

It should be noted that it is only the inward movement of the slats 128 that compresses the body part 138 to a diameter that permits its removal through the trocar 21; the TCE 120 does not force the body part 138 into the trocar 21, nor into any tube of a fixed diameter for that matter, in order to compress the body part 138.

Alternatively, once the body part 138 is disposed within the "skirt", the surgeon can keep the retrieval means 136 engaged with the body part 138 and then pull the TCE 120/retrieval means 136 together up through the trocar 21, thereby driving the slats 128 inward to compress the body part 138.

Furthermore, where the body part to be removed is elongated (not shown), it may not even be necessary to insert any retrieval means 136; rather, the surgeon would dispose the skirt over one end of the elongated body part so that a substantial portion of the body part is within the skirt. The surgeon would then simply pull upward on the TCE 120, thereby seizing while compressing the body part within the slatted lower portion 124.

Figure 10:
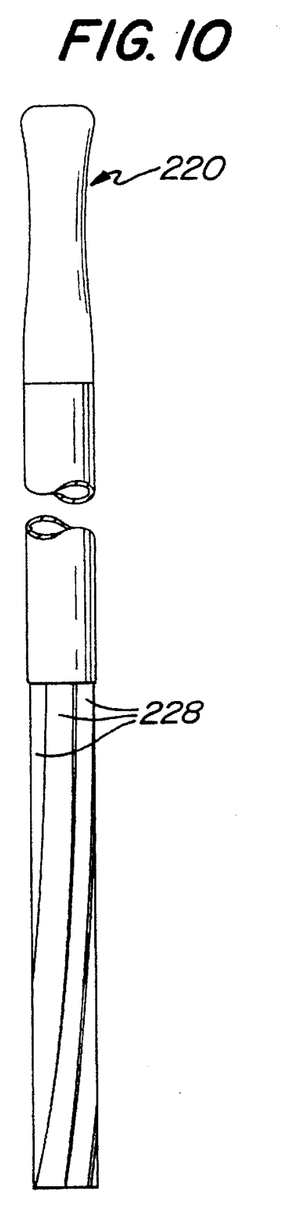
FIG. 10 is a diagram of the second embodiment of the present invention using overlapping swirled slats shown in the compressed condition.

In FIG. 10, there is shown a similar slatted TCE 220, that operates in the same manner as the TCE 120, but utilizes swirled slats 228, rather than the straight slats 128 of the TCE 120. In particular, FIG. 10 depicts the swirled slatted TCE 220 in the compressed state.

Figure 11:
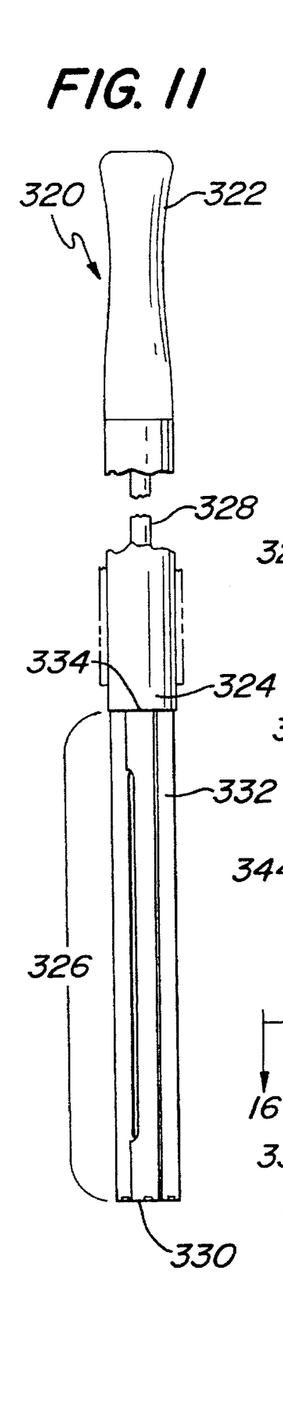
FIG. 11 is a diagram of a third embodiment of the present invention using pliable slats that are bowed to retrieve the body part.
Figures 12, 16:
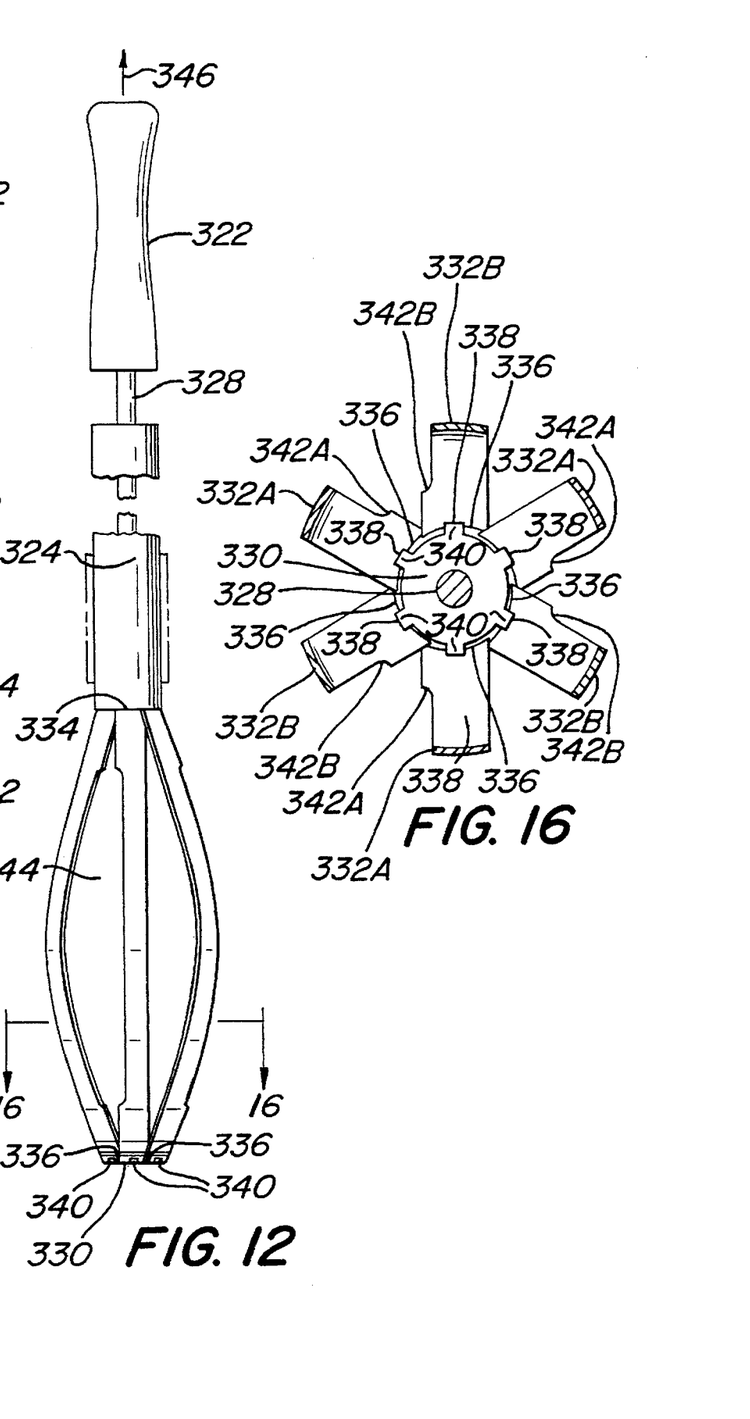
FIG. 12 is a diagram of the third embodiment shown in an open condition.
FIG. 16 is a cross-sectional view taken along line 16—16 of FIG. 12.

A third embodiment of the present invention is shown at 320 in FIGS. 11–12. The TCE 320 comprises an upper handle grip portion 322, a stationary lower housing 324 and a compression cage 326. A control rod 328 is coupled to the lower end of the upper handle grip portion 322. This control rod 328 passes through, and is slidable within, the stationary lower housing 324 and is coupled to a an endplate 330 at the bottom of the compression cage 326.

The compression cage 326 comprises a plurality of slats 332, each of which are fixedly secured at their top ends to the lower end 334 of the stationary lower housing 324. The bottom ends 336 of the slats 332 comprise recesses 338 that engage respective protrusions 340 distributed around the circumference of the endplate 330.

Figures 13, 14, 15:
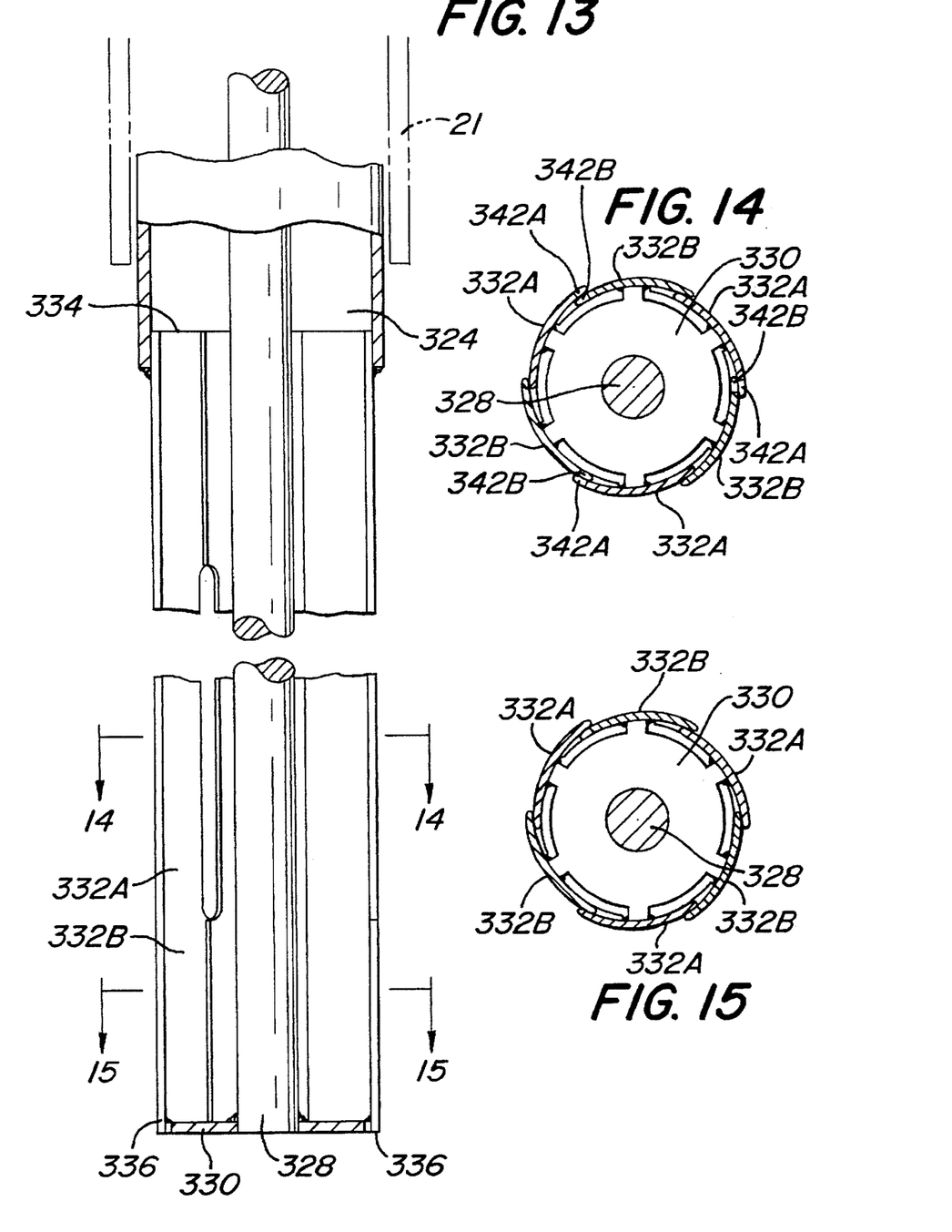
FIG. 13 is an enlarged side elevation partially broken showing the pliable slats in a closed condition.
FIG. 14 is a cross-sectional view taken along line 14—14 of FIG. 13.
FIG. 15 is a cross-sectional view taken along line 15—15 of FIG. 13.

As shown most clearly in FIG. 16, alternate adjacent slats (e.g., 332A and 332B) have matching recesses 342A and 342B that form a thin elongated oval whenever the compression cage 326 is in a compressed condition (FIGS. 11 and 13). In addition, in the compressed condition, the slats 332 overlap as shown in FIGS. 13–15. Whenever the compression cage 326 is in an open condition (FIGS. 12 and 16), these recesses 342A and 342B act to provide a greater opening 344 (FIG. 12) for permitting the entrance of the body part (not shown) that is to be compressed and removed.

Operation of the TCE 320 is as follows: Since the normal state of the TCE 320 is in the uncompressed state (FIG. 11), the surgeon inserts the compression cage 326 down into the trocar 21 until it is clear of the trocar 21 (FIG. 12). Once the compression cage 326 is disposed adjacent the body part (not shown), the surgeon grasps the portion of the stationary lower housing 324 that emerges upward from the trocar 21 with one hand, while pulling upward on the upper handle grip portion 322 with the other hand. This action causes the control rod 30 to push upward (in the direction 346), thereby forcing the endplate 330 to drive the bottom end 336 of the slats 332 upward. Since the upper ends of the slats 332 are fixedly secured to the lower end 334 of the stationary housing 324, all of the slats 332 bow outward, as shown in FIG. 12. This bowing action creates a "cage" that surgeon uses to capture the body part (not shown) that is to be compressed and removed. Once the body part is within the "cage", the surgeon releases the upward force on the upper handle grip portion 322. This action allows the slats 332 to be restored to their normal uncompressed condition while compressing the body part down to the approximate diameter of the endplate 330 (FIGS. 14–15). The compressed body part can then be removed with the TCE 320 from the trocar 21.

It should be understood that each of the slats 332 comprises a material of sufficient rigidity such that the restoring force can compress a large variety of materials confined inside the compression cage 326.

Without further elaboration, the foregoing will so fully illustrate my invention that others may, by applying current or future knowledge, readily the same for use under various conditions of service.

I claim:

1. An apparatus for compressing and extracting internal body parts to be removed from a patient, said apparatus comprising:

means for encompassing and compressing an internal body part to be removed, said means including relatively movable overlapping sections provided by a single layer of material wound into a helix, said overlapping sections forming walls of a variable-sized chamber, said walls being of sufficient rigidity for compressing the body part to a size permitting the removal of the compressed body part from the body; and actuation means, said means fixedly attached to said encompassing and compressing means, for tightening said helix to reduce the size of said chamber and to compress the internal body part.

2. The apparatus of claim 1 wherein said single layer of material includes parallel edges each having a respective recess positioned at a respective predetermined position therein, said parallel edges being controllable to align said respective recesses to form an aperture.

* * * * *